US009848819B2

(12) United States Patent
Kezirian et al.

(10) Patent No.: US 9,848,819 B2
(45) Date of Patent: Dec. 26, 2017

(54) AIRFLOW AND AIRWAY FACTORS

(71) Applicants: Eric James Kezirian, Los Angeles, CA (US); David Andrew Wellman, Wayland, MA (US)

(72) Inventors: Eric James Kezirian, Los Angeles, CA (US); David Andrew Wellman, Wayland, MA (US)

(73) Assignee: Eric James Kezirian, Los Angeles, CA (US)

( * ) Notice: Subject to any disclaimer, the term of this patent is extended or adjusted under 35 U.S.C. 154(b) by 176 days.

(21) Appl. No.: 14/715,829

(22) Filed: May 19, 2015

(65) Prior Publication Data
US 2015/0327806 A1 Nov. 19, 2015

Related U.S. Application Data

(60) Provisional application No. 62/000,477, filed on May 19, 2014.

(51) Int. Cl.
*A61B 5/08* (2006.01)
*A61B 5/00* (2006.01)
*A61B 5/085* (2006.01)
*A61B 5/087* (2006.01)

(52) U.S. Cl.
CPC ............ *A61B 5/4815* (2013.01); *A61B 5/085* (2013.01); *A61B 5/087* (2013.01); *A61B 5/4818* (2013.01); *A61B 5/7282* (2013.01)

(58) Field of Classification Search
CPC ...... A61B 5/087; A61B 5/4818; A61B 5/7282
See application file for complete search history.

(56) References Cited

U.S. PATENT DOCUMENTS

2002/0007127 A1* 1/2002 Sullivan ................ A61B 5/097
600/529

* cited by examiner

*Primary Examiner* — Christian Jang
(74) *Attorney, Agent, or Firm* — Brooks Kushman P.C.

(57) ABSTRACT

A method for characterizing sleep disordered breathing may include identification of at least one of a plurality of predefined airway structural sources associated with a sleep disordered breathing event based on airflow data. In one example, an identification of at least one of a plurality of predefined airway structural sources associated with a sleep disordered breathing event is made based on data indicative of a ratio of a difference between a peak inspiratory airflow rate and a mid-inspiratory airflow rate to the peak inspiratory airflow rate captured during occurrence of the sleep disordered breathing event.

15 Claims, 14 Drawing Sheets

AIRFLOW AND AIRWAY FACTORS

CROSS-REFERENCE TO RELATED APPLICATION

This application claims the benefit of U.S. Provisional Application No. 62/000,477, filed May 19, 2014, the contents of which are hereby incorporated by reference in their entirety.

BACKGROUND

Sleep disordered breathing, including snoring and obstructive sleep apnea, affects tens of millions of adults in the United States. It is associated with substantial cardiovascular morbidity and mortality, endocrine disturbances, excessive daytime sleepiness, quality of life and performance deficits, and motor vehicle crashes.

Sleep disordered breathing may be associated with decreased airflow during sleep or snoring related to vibration of structures of the head and neck. One or more anatomical structures or factors may contribute to sleep disordered breathing, and these structures may contribute to sleep disordered breathing in different patterns or configurations, resulting in subtypes of structure-specific contributions. Many sleep disordered breathing treatments are anatomical structure- (and, possibly, subtype-) or factor-specific, and the variation in contributing anatomical structures or factors among patients may lead to variable success rates for many treatments.

Patients with sleep disordered breathing may undergo a sleep study that measures a number of signals, including airflow. Current approaches of sleep study signal analysis may not characterize (1) the anatomical structures or factors contributing to sleep disordered breathing or (2) the site of sound production, and they may not be associated with outcomes of specific treatments. Existing invasive and non-invasive upper airway examination techniques also may not provide this information.

There is enthusiasm among clinicians and patients alike for an improved ability to characterize the anatomical structures (including subtypes) or factors contributing to sleep disordered breathing or the site of sound production and to guide the selection of treatments.

SUMMARY

Certain embodiments may, for example, determine the anatomical structures (with possible subtypes) or factors contributing to sleep disordered breathing with analysis of airflow. These embodiments may, for example, improve treatment selection for patients with sleep disordered breathing.

DETAILED DESCRIPTION

As required, embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details. Therefore, specific details disclosed herein are not to be interpreted as limiting, but merely as a representative basis for teaching one skilled in the art to employ variously the present invention.

Sleep disordered breathing can occur due to a combination of mechanisms, including anatomy, negative pressure within the airway, changes in muscle activation, changes in lung volumes, and instability of ventilatory control. One or more of these mechanisms may play an important role in an individual patient, and a mechanism may have more than one subtype. For example, one or more anatomical structures (structural sources) or factors may contribute to sleep disordered breathing in an individual patient.

The upper airway is surrounded by a number of anatomical structures that can contribute to sleep disordered breathing. Those structures may include the nasal soft tissues; turbinates, sinuses; nasal septum; maxilla and hard palate; mandible; soft palate; palatine tonsils; pharyngeal lateral walls; tongue and lingual tonsil; epiglottis; and larynx. The laryngopharynx extends from the nasopharynx (containing the adenoid) to the larynx (containing the vocal cords), and structures in the laryngopharynx that may contribute to sleep disordered breathing include the soft palate, pharyngeal lateral walls, tongue, and epiglottis. More than one anatomical structure may contribute to sleep disordered breathing in an individual patient.

Fiberoptic endoscopic examination of the upper airway may be performed during different states (e.g., wakefulness, natural sleep, and sedation). A flexible endoscope may be passed through the nasal cavity into the pharynx. Fiberoptic endoscopic examination permits direct visualization of the upper airway, including evaluation of specific anatomical structures or factors that may contribute to sleep disordered breathing.

Figure 1A:
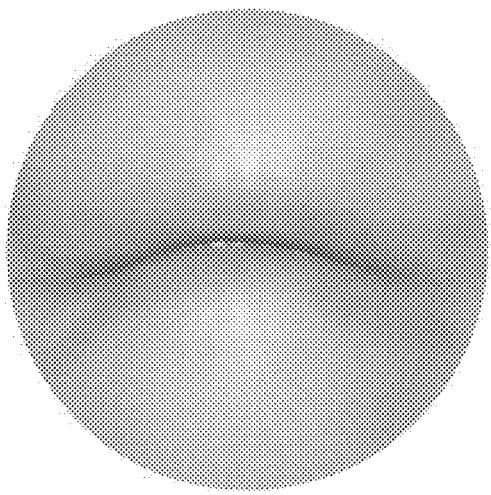
FIG. 1A is an illustration of the endoscopic view of airway narrowing related to the palate.
Figure 1B:
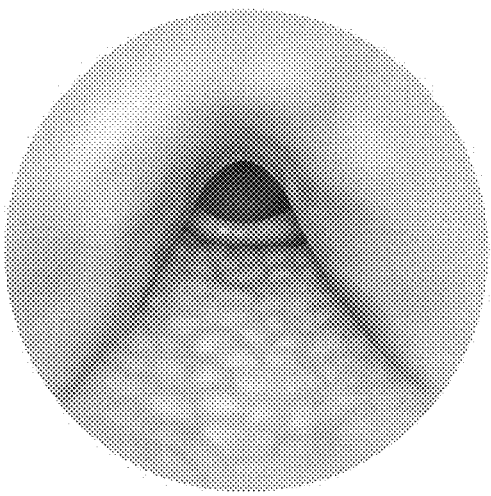
FIG. 1B is an illustration of the endoscopic view of airway narrowing related to the pharyngeal lateral walls.
Figure 1C:
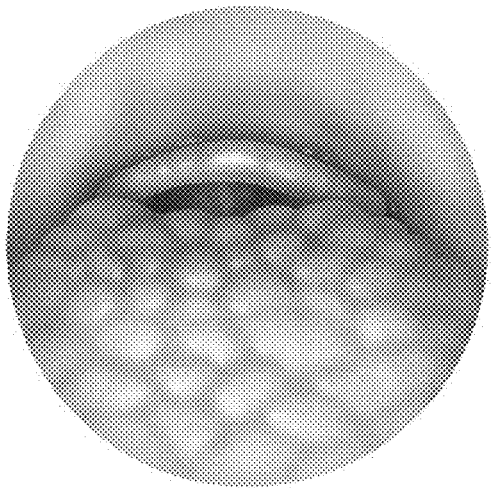
FIG. 1C is an illustration of the endoscopic view of airway narrowing related to the tongue.
Figure 1D:
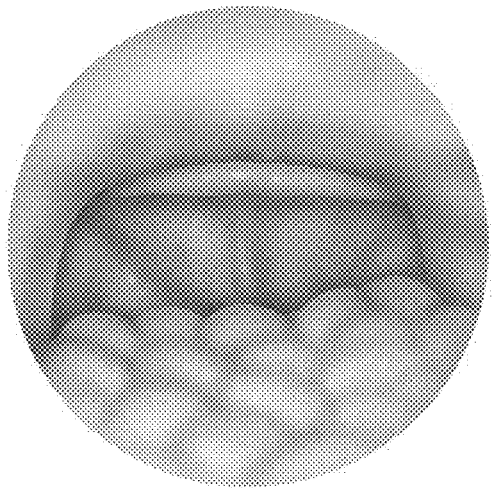
FIG. 1D is an illustration of the endoscopic view of airway narrowing related to the epiglottis.

Referring to FIGS. 1A-1D, it is possible to visualize airway obstruction related to the soft palate (FIG. 1A), pharyngeal lateral walls (FIG. 1B), tongue (FIG. 1C), or epiglottis (FIG. 1D). There may be other appearances to sleep disordered breathing related to these structural sources of sleep disordered breathing, including those associated with differences in the configuration of airway narrowing or obstruction. For example, the soft palate may contribute to airway obstruction in an anteroposterior (shown in FIG. 1A), lateral, or concentric (combination of anteroposterior and lateral) configuration. As another example, the epiglottis may contribute to airway obstruction in an anteroposterior (shown in FIG. 1D) or lateral configuration.

A sleep study or other evaluation during wakefulness, natural sleep, or sedation may include monitoring or measurement of signals, including one or more of the following: airflow, hemoglobin oxygen saturation, sound (generally snoring), body position, electrocardiogram, electroencephalogram, and electrooculogram. These signals may undergo filtering (e.g., based on frequency), smoothing, or other signal processing before or after analysis. These signals may differ in an individual between breaths or from one individual to another. The variation from one individual to another may exist among individuals who are otherwise grouped together according to current approaches of sleep study signal analysis (e.g., similar values of the apnea-hypopnea index that quantifies the frequency of disordered breathing events). For example, individuals may demonstrate airflow patterns that may be characterized by a set of airflow parameters, such as the initial inspiratory peak airflow rate, peak inspiratory airflow rate, plateau airflow rate, mid-inspiratory airflow rate, difference between initial peak inspiratory airflow rate and plateau airflow rate, difference between peak inspiratory airflow rate and mid-inspiratory airflow rate, initial expiratory airflow rate, airflow rate at other segments of the respiratory cycle, frequency of variation in airflow rate, amplitude of variation in airflow rate, stability of the peak airflow across breaths, and patterns of decrements in magnitudes of peak or plateau airflow. The plateau airflow rate may be defined by the airflow rate at mid-inspiration, but other definitions may be used if there is variation in the airflow rate at mid-inspiration or other portions of the inspiratory cycle. Airflow may also be characterized by patterns (e.g., shapes) that do not correspond to specific parameters. Similar or different airflow parameters or patterns may be evaluated for inspiration and expiration; for stable breathing; or before, during, or after disordered breathing events.

Figure 2:
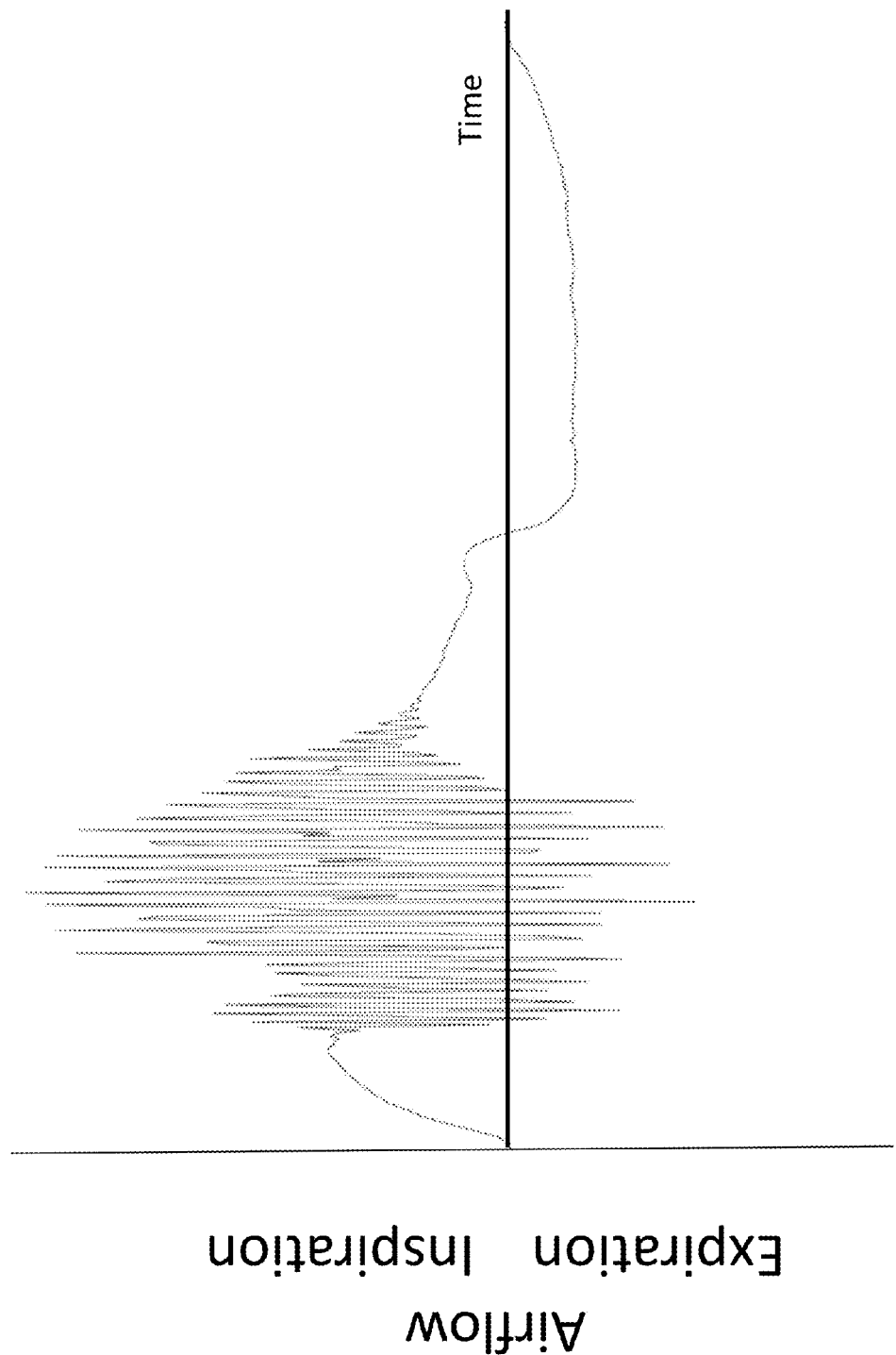
FIG. 2 is a possible airflow tracing.

Referring to FIG. 2, airflow monitoring may occur during sleep. For example, a sleep study is commonly performed in the evaluation of sleep disordered breathing, and it measures airflow during natural sleep. An airflow signal may demonstrate characteristics that can be measured in other signals. For example, airflow may include variations that may be related to vibration of structures or sound that can be measured in a sound signal.

Figure 3:
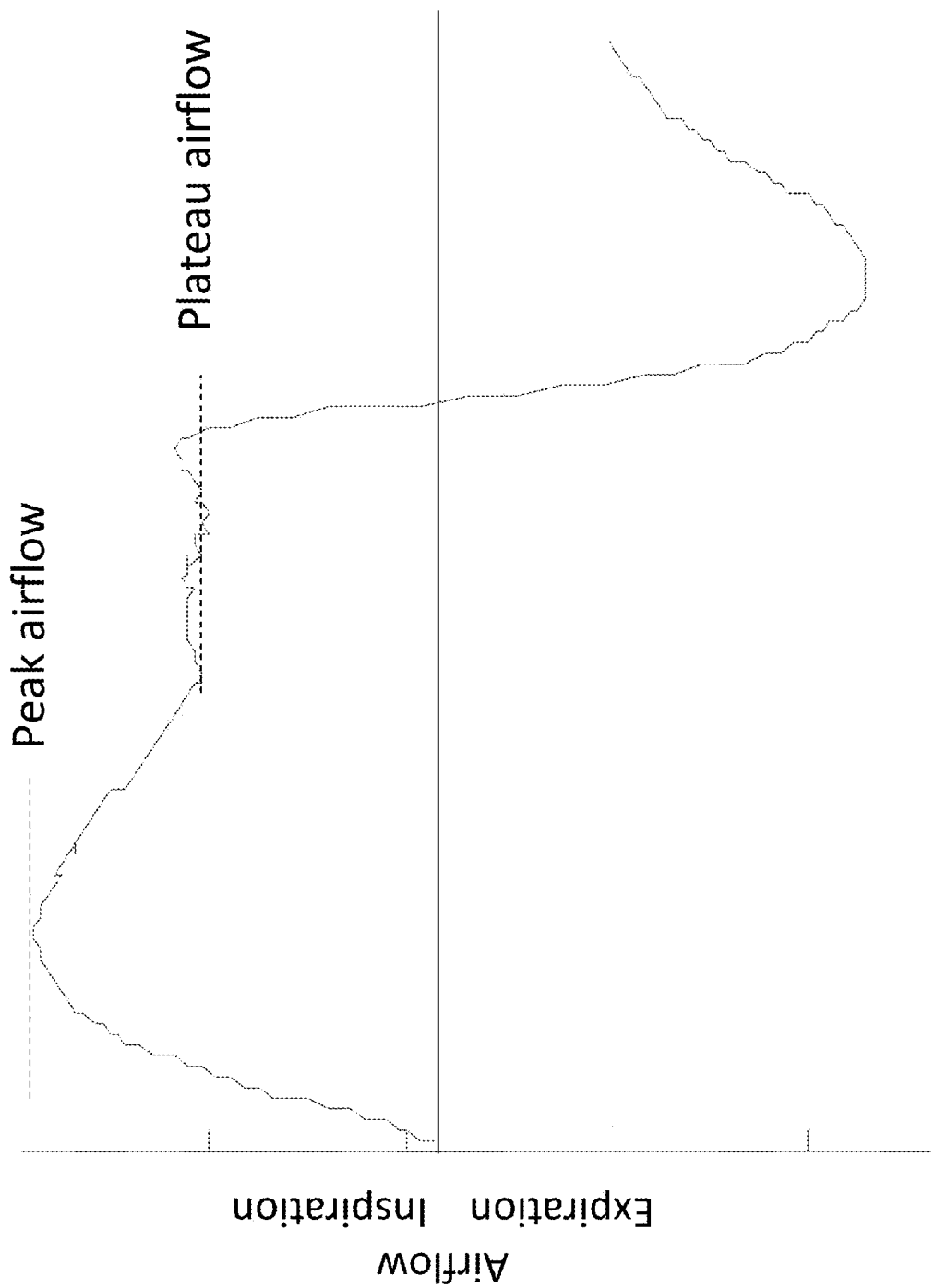
FIG. 3 is another possible airflow tracing.

Referring to FIG. 3, airflow may demonstrate different patterns, whether for different individuals or the same individual during different breaths. Airflow may be characterized with a peak airflow and plateau airflow, in addition to other parameters described elsewhere in this application. Because airflow may not reach a stable rate, as in FIG. 5, the plateau airflow rate may also be defined as airflow rate at the midpoint of inspiratory cycle (mid-inspiratory airflow rate). A number of analyses may be performed on airflow tracings, including calculation of the ratio of peak airflow rate less plateau airflow rate to peak airflow rate. The ratio may represent the degree of negative effort dependence, in which there are decreases in airflow associated with increased inspiratory effort. Airflow analysis may include determination of other airflow parameters, including total airflow during inspiration. Airflow parameters may be determined before or after signal processing (filtering, smoothing, etc.). Airflow analysis may evaluate all breaths or a subset (e.g., breaths with partial decrease in airflow, absence of airflow, prior to and/or after changes in airflow, normal airflow, etc.).

Figure 4:
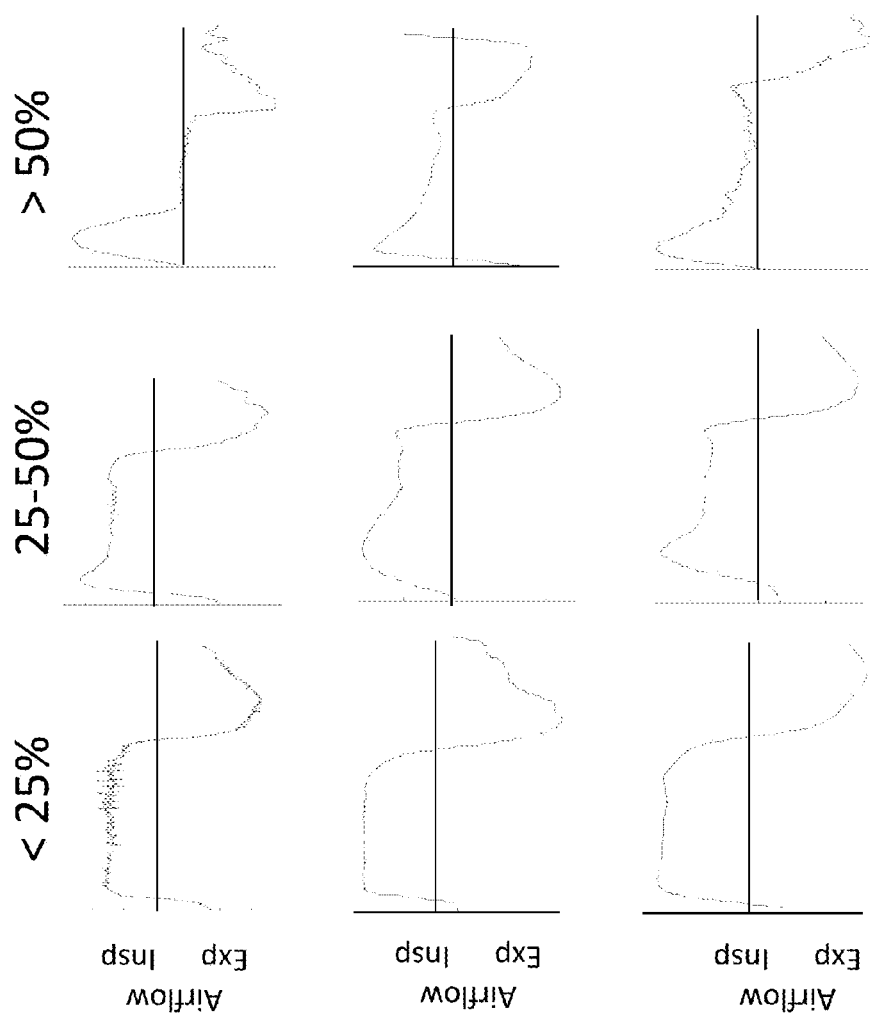
FIG. 4 is a series of possible airflow tracings.

Referring to FIG. 4, airflow analysis can identify differences in the ratio of peak inspiratory airflow rate less plateau airflow rate to peak airflow rate between individuals or between breaths for the same individual. Similar differentiation may be possible with other airflow parameters or patterns or other signals.

An embodiment may determine the anatomical structures (structural sources) or factors contributing to sleep disordered breathing using analysis of airflow rate. Another embodiment may determine the anatomical structures or factors contributing to sleep disordered breathing with more than one airflow parameter. More than one anatomical structure or factor may contribute to sleep disordered breathing in an individual patient.

Figure 5:
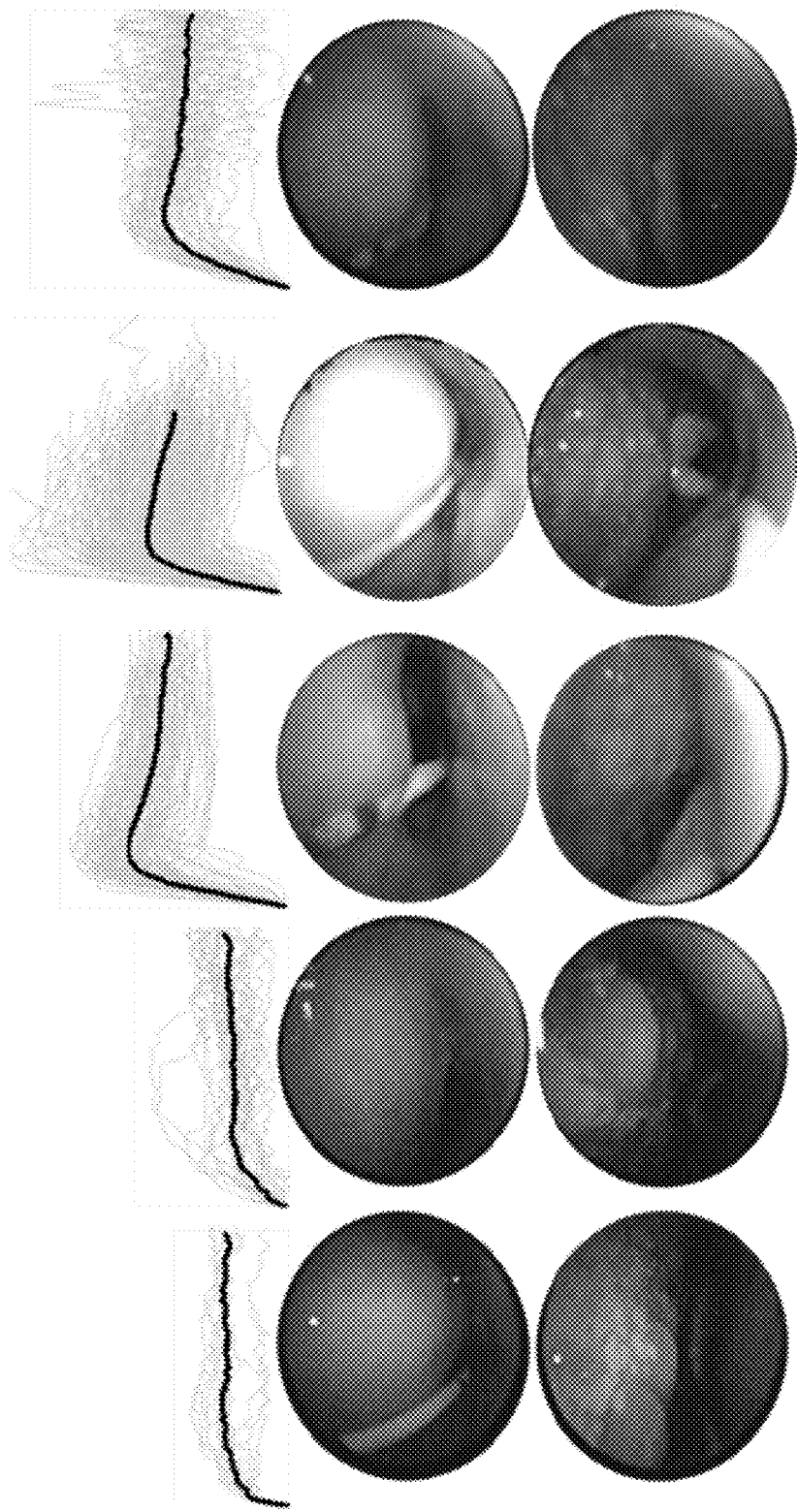
FIG. 5 shows possible airflow tracings and endoscopic images associated with tongue contribution to airway obstruction.
Figure 6:
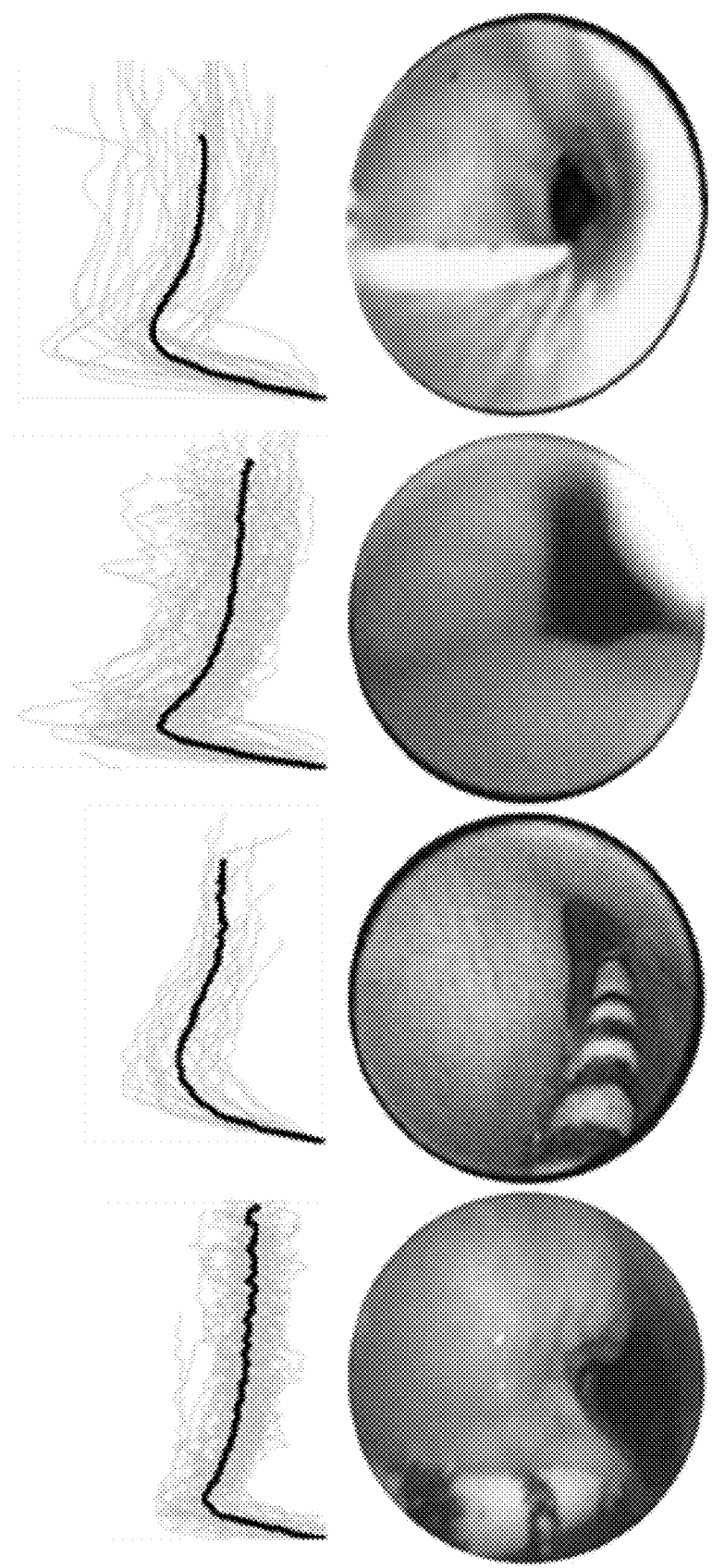
FIG. 6 shows possible airflow tracings and endoscopic images associated with palate contribution to airway obstruction.
Figure 7:
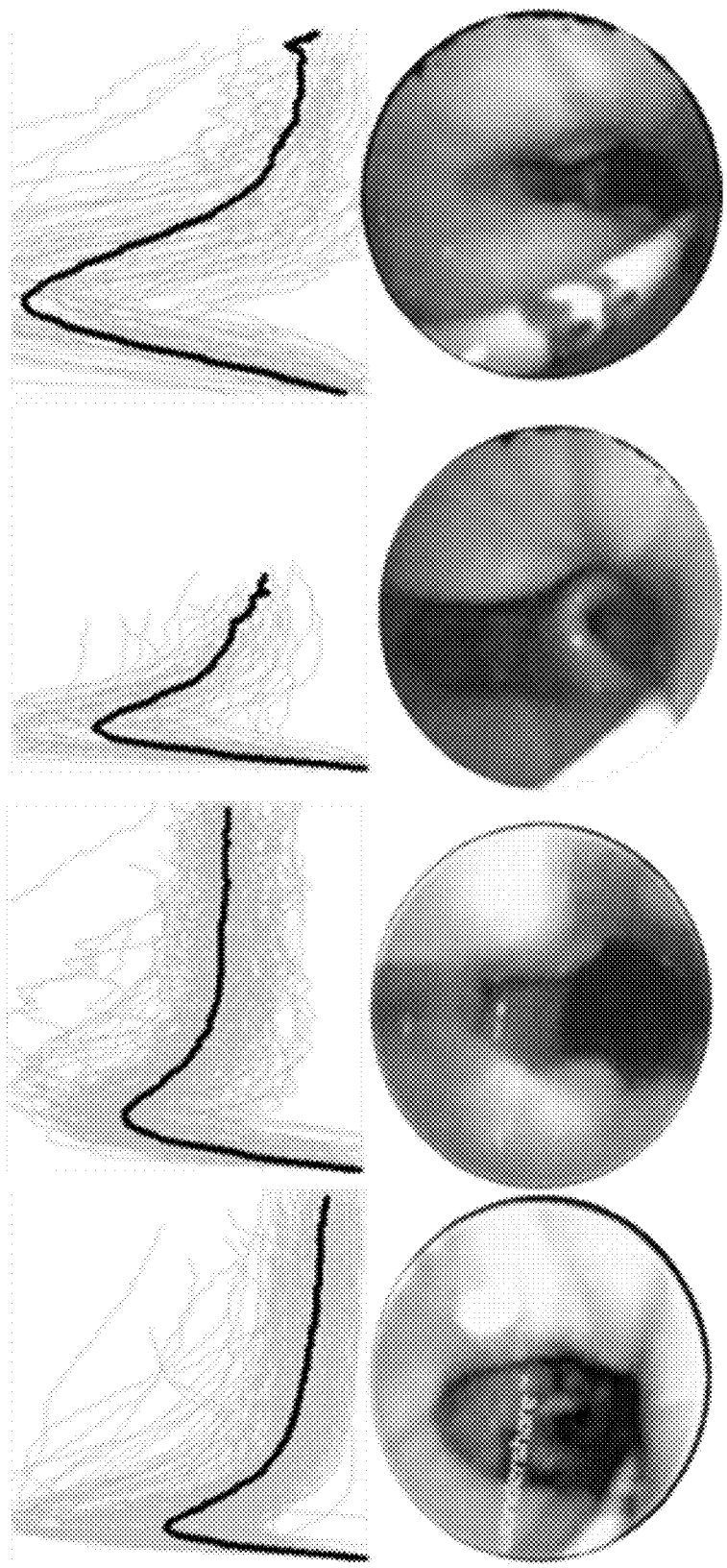
FIG. 7 shows possible airflow tracings and endoscopic images associated with lateral pharyngeal wall contribution to airway obstruction.

Different anatomical structures or factors may contribute to airway obstruction in different patients. During inspiration, the airway may narrow due to different anatomical structures As such, airflow analysis can generate airflow parameters that may provide information about the anatomical structures or factors contributing to sleep disordered breathing. Referring to FIGS. 5-7, the top row of tracings show inspiratory airflow tracings for different disordered breathing events grouped for individuals, with the average airflow pattern across the events shown with a darker line. Referring to FIG. 5, below each airflow tracing are endoscopic images for the same individual, viewing the superior portion of the laryngopharynx (nasopharynx/oropharynx that is behind the soft palate, or retropalatal region) in the top row of images and the inferior portion of the laryngopharynx (oropharynx/hypopharynx/larynx, or retrolingual region) in the bottom row of images. The tongue may be more likely to demonstrate a low decrease from peak airflow rate in early inspiration to the mid-inspiratory plateau airflow rate when it contributes to sleep disordered breathing. This may be due to its collapsibility and low negative effort dependence. The tongue may narrow the airway in an anteroposterior dimension, moving posteriorly against the palate to narrow the retropalatal airway.

Referring to FIGS. 6 and 7, images from the inferior portion of the laryngopharynx only are shown below the airflow tracings. Referring to FIG. 6, the palate may be more likely to demonstrate a decrease from peak airflow rate in early inspiration to the mid-inspiratory plateau airflow rate when it contributes to sleep disordered breathing that is greater than for the tongue. This may be due to its collapsibility and greater negative effort dependence. There may be differences in the magnitude of the decrease from peak inspiratory airflow rate to mid-inspiratory plateau airflow rate based on the configuration (anteroposterior, lateral, or concentric) of airway narrowing related to the palate. The palate may also be more likely to demonstrate marked changes in expiratory airflow rate due to greater collapsibility. Referring to FIG. 7, the pharyngeal lateral walls may be more likely to demonstrate a decrease from peak airflow rate in early inspiration to the mid-inspiratory plateau airflow rate when it contributes to sleep disordered breathing that is greater than for the tongue. This may be due to its collapsibility and greater negative effort dependence.

Figure 8:
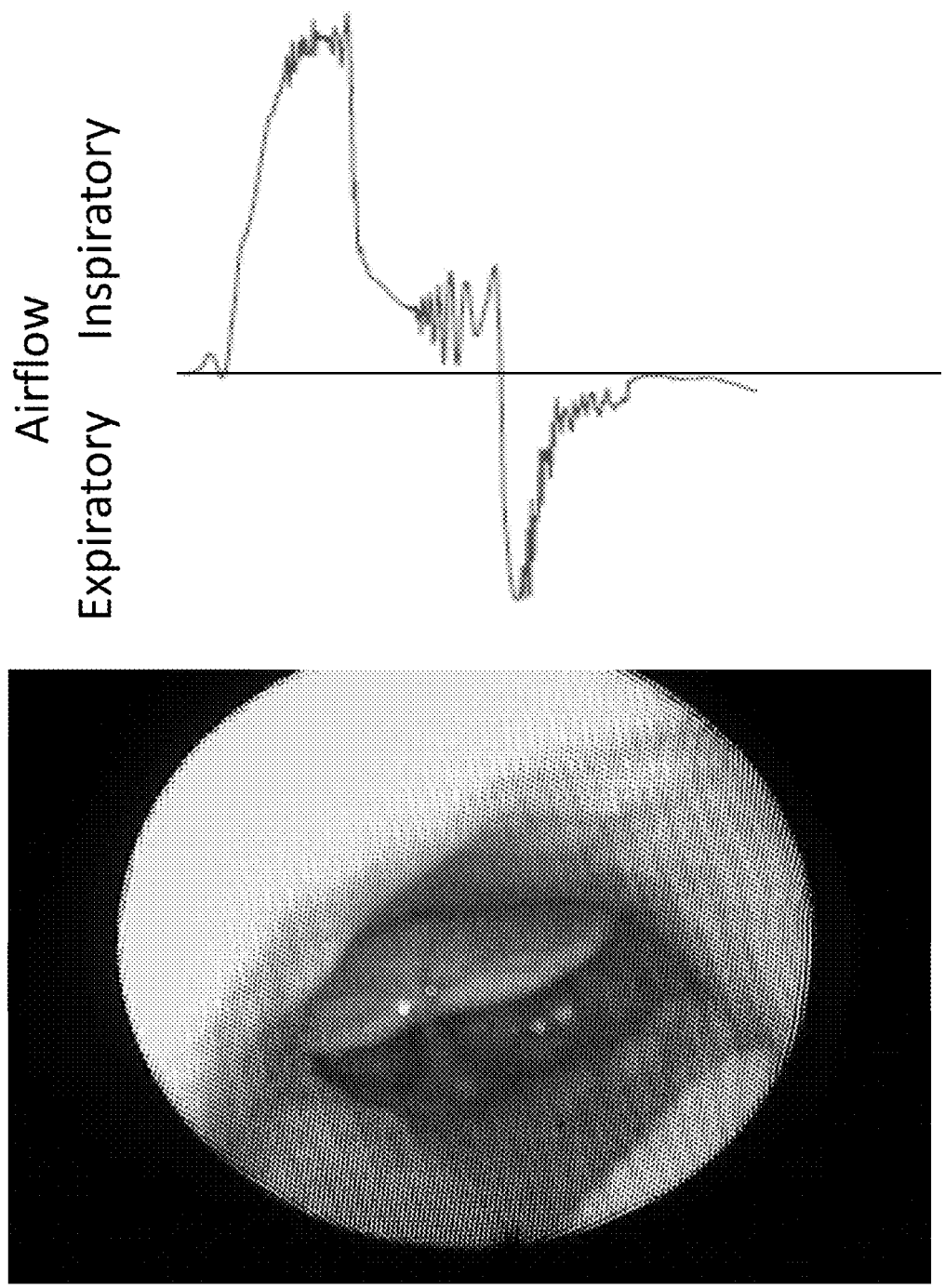
FIG. 8 shows a possible airflow tracing and endoscopic image associated with epiglottis contribution to airway obstruction.

Referring to FIG. 8, the epiglottis may be more likely to demonstrate a greater decrease from peak airflow rate in early inspiration to the mid-inspiratory plateau airflow rate when it contributes to sleep disordered breathing. In addition, the epiglottis may be more likely to demonstrate a greater rate of change of inspiratory airflow rate when it contributes to sleep disordered breathing. This may be due to its collapsibility and greater negative effort dependence. There may be differences in the magnitude of the decrease in airflow based on the configuration of epiglottic airway narrowing (anteroposterior or lateral).

Figure 9:
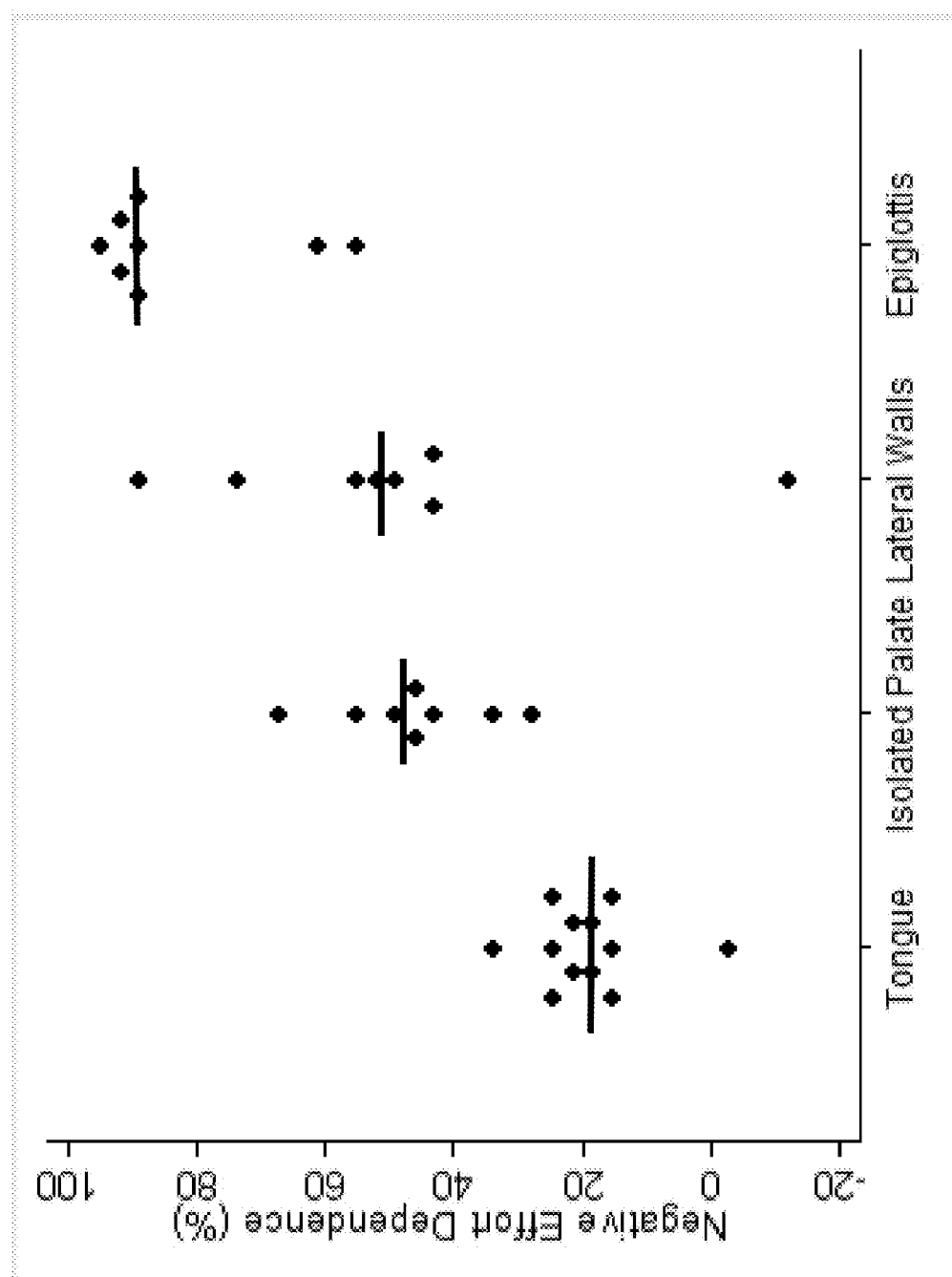
FIG. 9 shows values for negative effort dependence and structures contributing to airway obstruction.

Referring to FIG. 9, there may be an association between the negative effort dependence, defined as the peak inspiratory minus mid-inspiratory plateau airflow rates to peak airflow rate, and the structures and factors contributing to sleep disordered breathing. More than one structure or factor may contribute to sleep disordered breathing in an individual patient, whether during the same or different disordered breathing events. Airflow and other signals may reflect a combination of structures and factors contributing to sleep disordered breathing.

Figure 10:
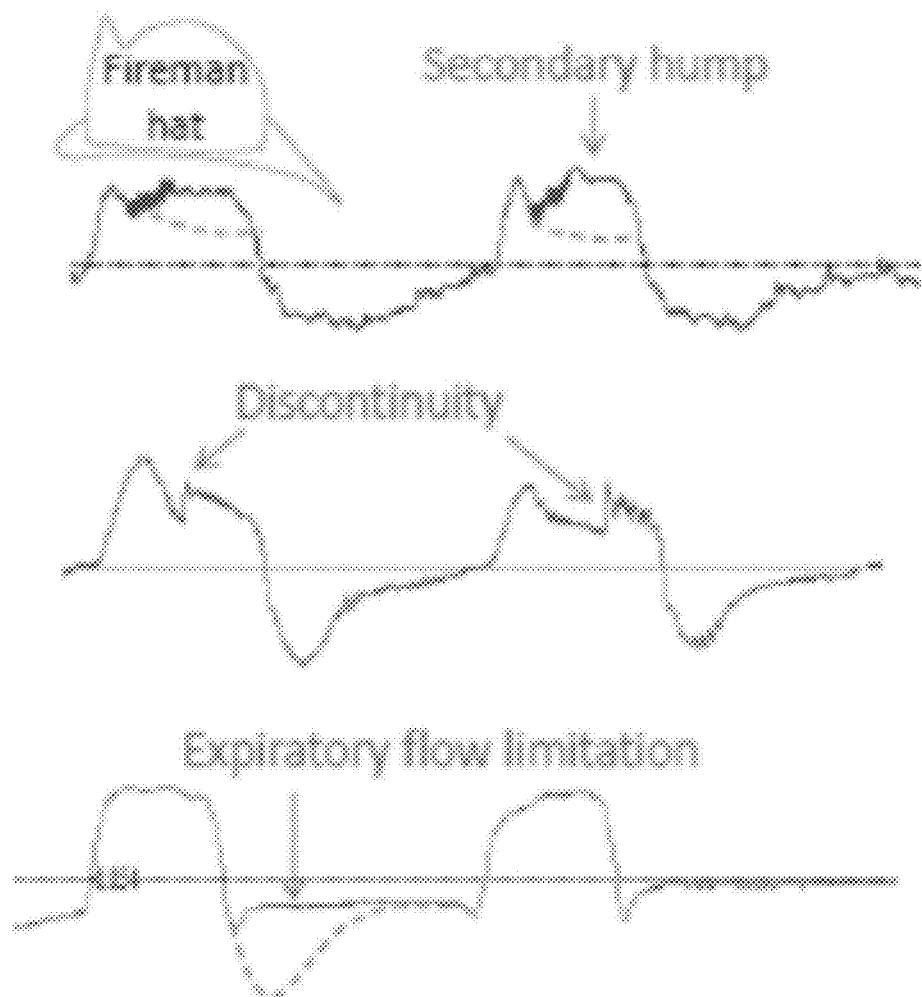
FIG. 10 shows other possible airflow tracings.

Other airflow features may be present, and these may relate to mechanisms or factors contributing to sleep disordered breathing. Referring to FIG. 10, a secondary hump in airflow occurring after an initial peak in airflow during inspiration, may occur due to opening of the airway that may be related to muscle activation during inspiration. The secondary hump is shown in the uppermost airflow tracing in a solid line relative to the dotted line of a typical airflow pattern that would be expected, based on the initial pattern of inspiratory airflow. Discontinuities in inspiratory or expiratory airflow (shown in middle airflow tracing) may occur with acute airway narrowing, such as may occur with palatal or epiglottic prolapse (see also FIG. 8). Discontinuities in expiratory airflow or other pronounced expiratory airflow limitation (shown in the lowest airflow tracing as a solid line and compared to dotted line for normal expiratory airflow that would be expected) can also occur and may be related to palatal prolapse. There may be interactions between anatomic structures (e.g., palate and tongue) that may affect the airflow characteristics or degree of palatal vibration (e.g., less vibration with a greater degree of coupling between the structures).

Figure 11:
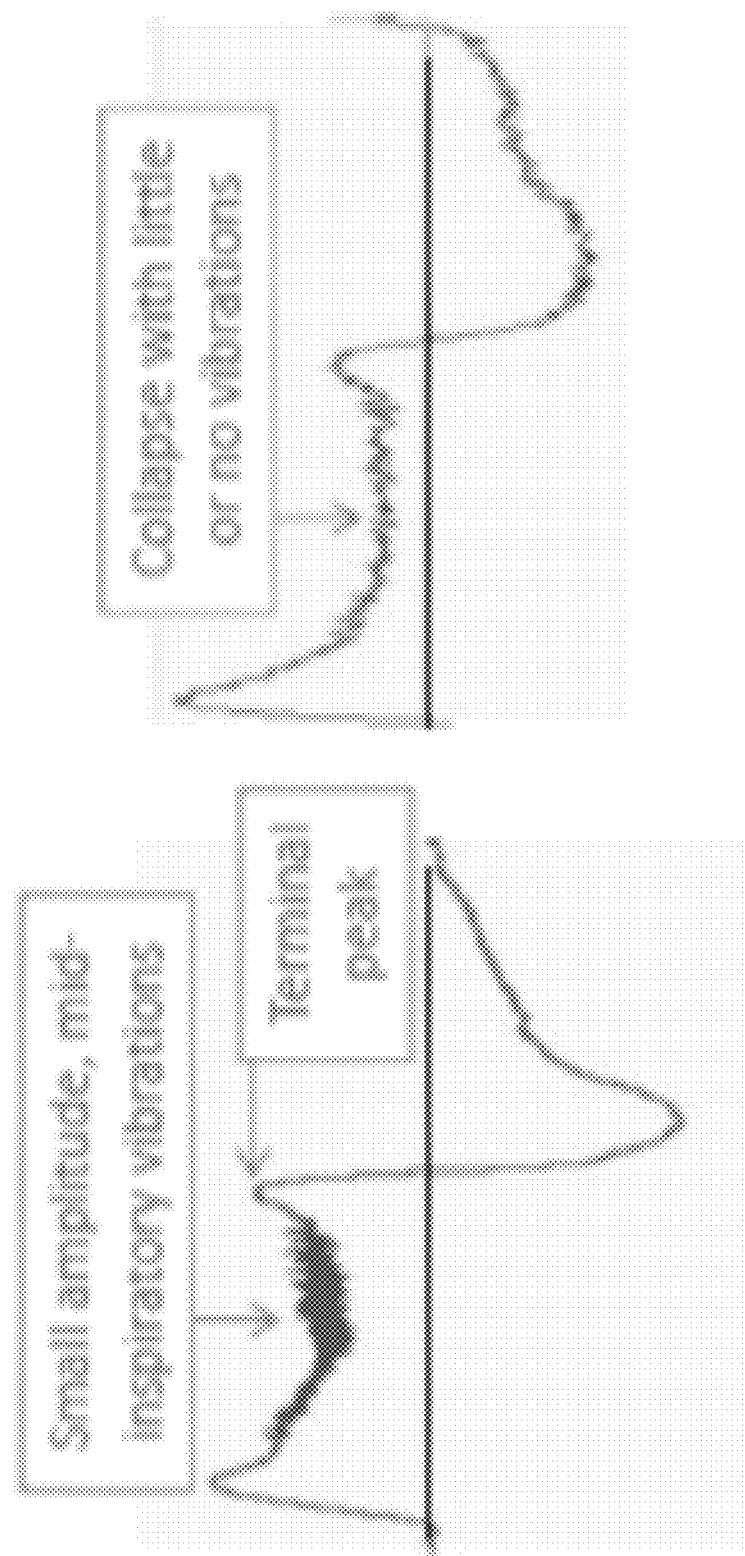
FIG. 11 shows other possible airflow tracings.

Referring to FIG. 11, different anatomic structures or mechanisms may produce different vibrations or variations in airflow (characterized by frequency, amplitude, duration, timing relative to the respiratory cycle, increase in airflow rate towards the end of inspiration, etc.) or other signals (e.g., sound). A terminal peak in inspiratory airflow may be a marker of airway elasticity or airway opening.

Figure 12:
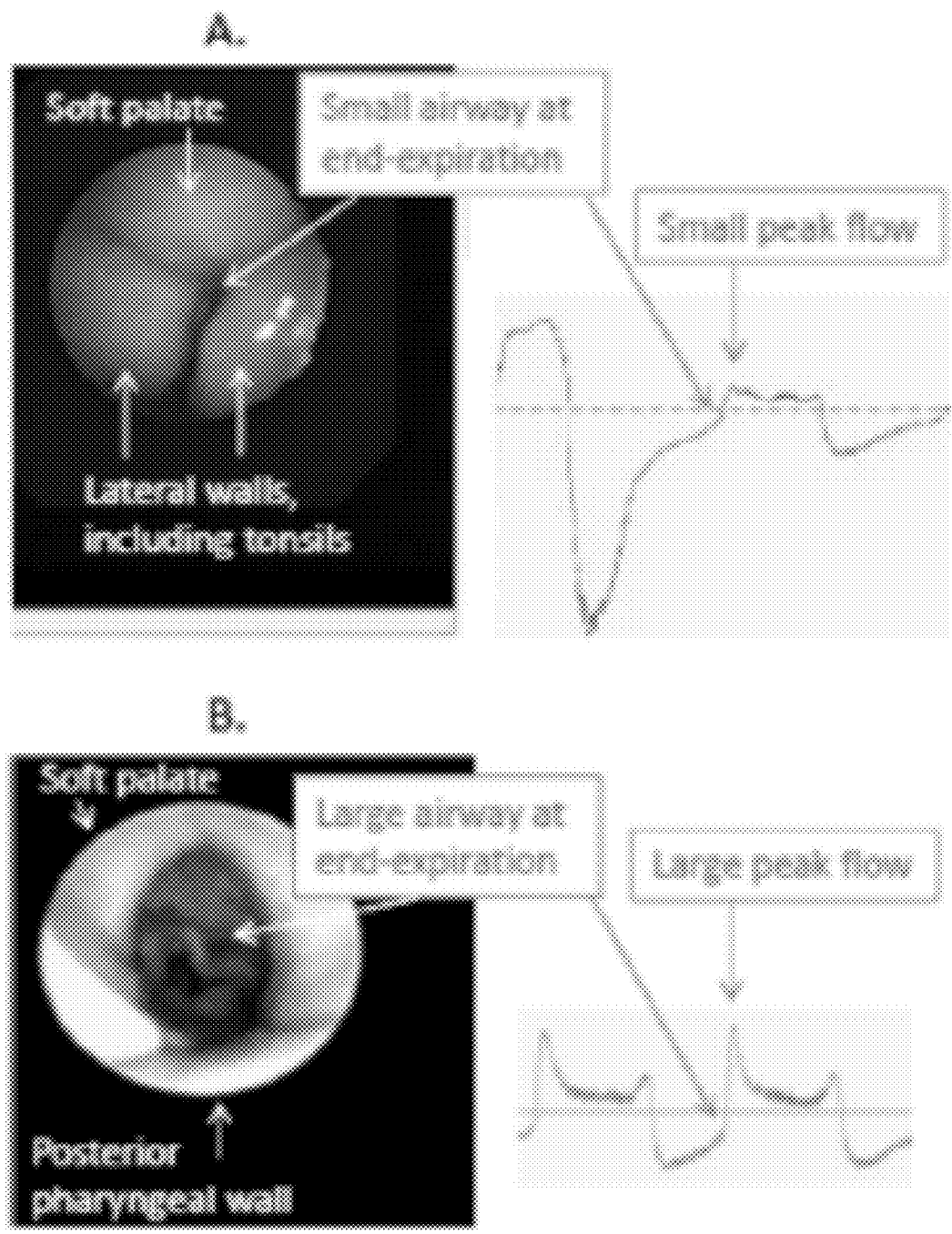
FIG. 12 shows other possible endoscopic images and airflow tracings.

Referring to FIG. 12, the magnitude of peak inspiratory airflow may be associated with the degree of airway obstruction or airway dimensions. For example, a greater degree of airway obstruction (smaller airway, shown in the image on the upper left) may indicate a lesser rate of peak airflow (shown in the airflow tracing on the upper right), whether throughout the respiratory cycle or in certain periods (e.g., end-expiration or early inspiration). In contrast, a lesser degree of airway obstruction or airway dimensions (larger airway, shown in the image on the lower left) may indicate a greater rate of peak airflow (shown in the airflow tracing on the lower right). This association may be specific to individual structures and their contribution to airway obstruction in distinct regions of the airway (e.g., retropalatal or retrolingual regions).

Figure 13:
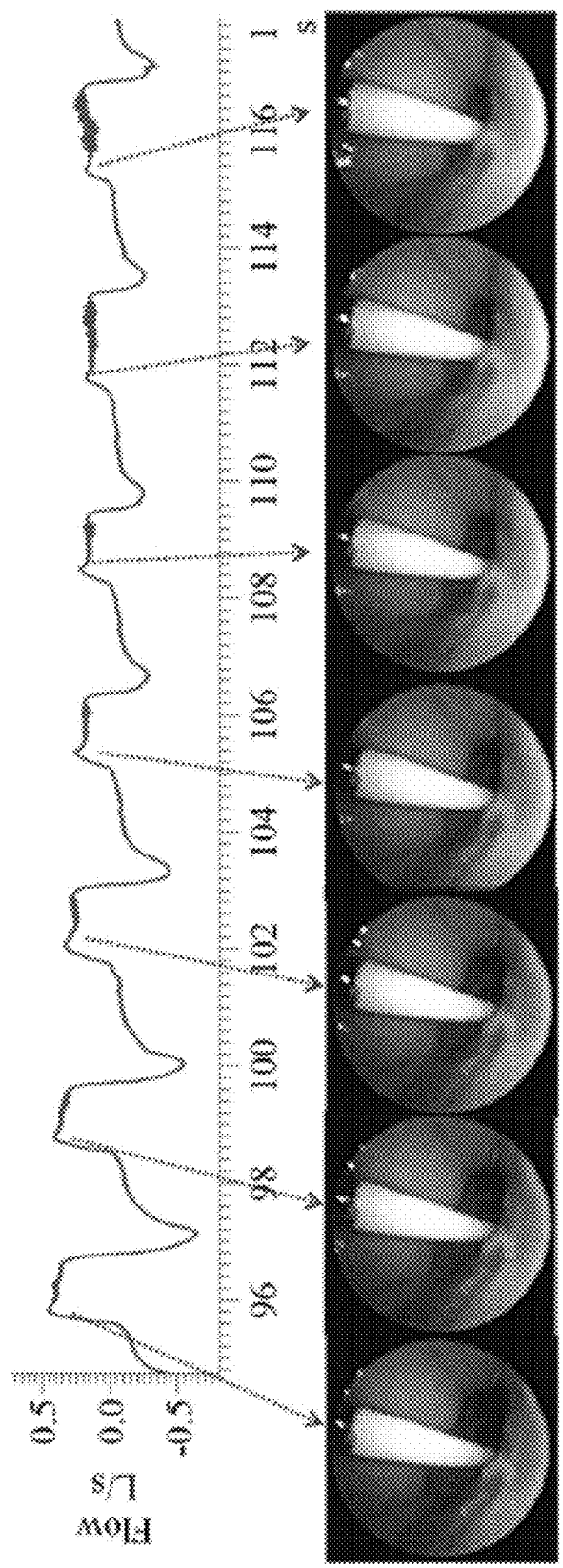
FIG. 13 shows other possible airflow tracings and endoscopic images.

Referring to FIG. 13, the magnitude of peak airflow may vary in an individual patient over successive breaths, with possible associated changes in airway dimensions at end-expiration. Shown is an airflow tracings and images of the retropalatal airway at end-expiration over successive breaths (with a catheter in place to calibrate airway area measurements), with decreased peak inspiratory airflow and decrease in retropalatal airway dimensions. There may also be an association with airway dimensions at other regions of the airway or other portions of the respiratory cycle. Other measures of airflow may also be associated with airway dimensions.

Figure 14:
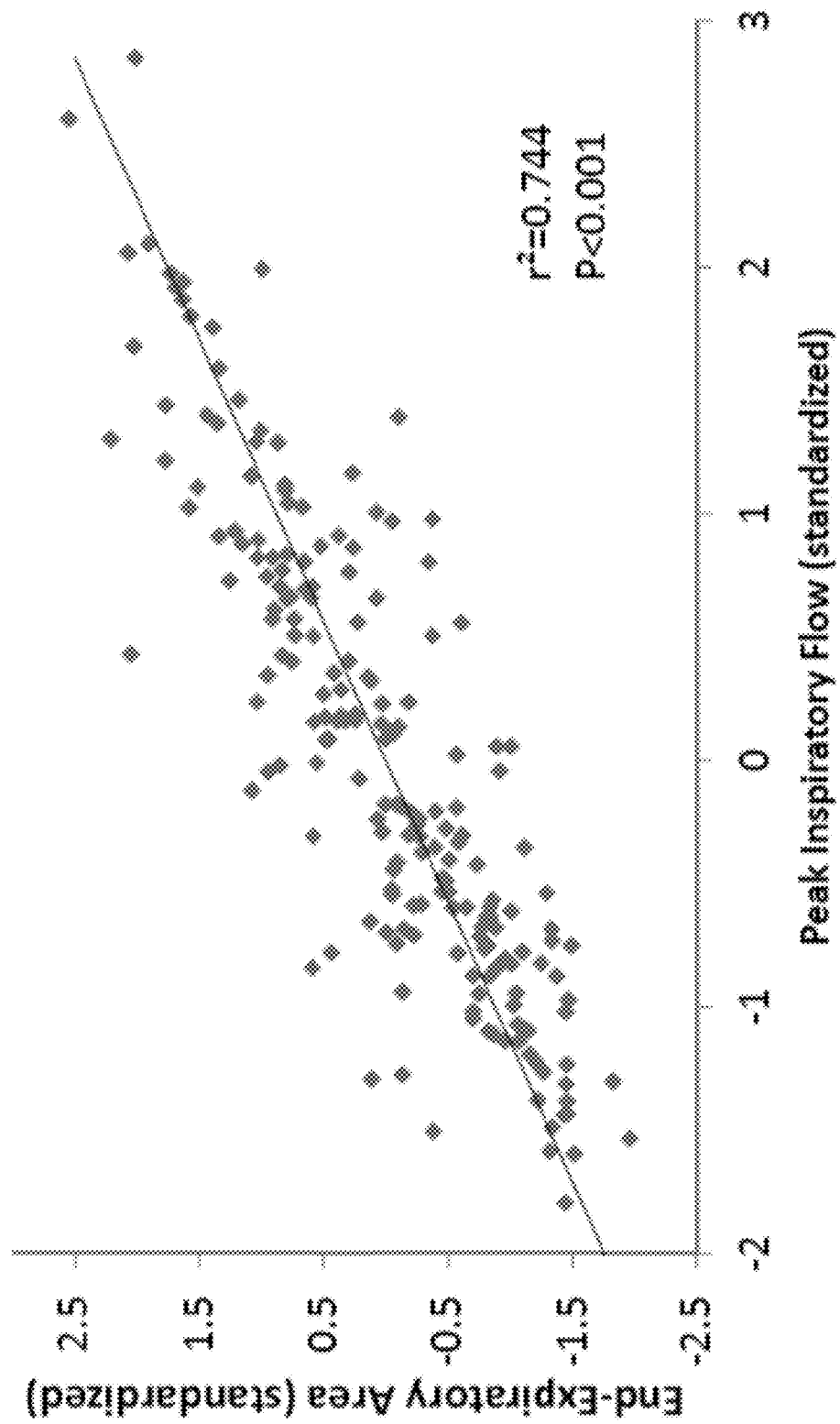
FIG. 14 shows values for end-expiratory retropalatal airway area and peak inspiratory airflow.

Referring to FIG. 14, there may be an association between the retropalatal airway dimension at end-expiration and the magnitude of peak inspiratory airflow in different patients and different breaths. There may also be an association between peak inspiratory airflow and retrolingual airway dimensions at end-expiration or with retropalatal or retrolingual airway area during other portions of the respiratory cycle. Differences in peak airflow for an individual patient may be associated with differences in relative or absolute airway dimensions. Other measures of airflow may also be associated with airway dimensions.

Analysis of sound, whether directly through the sound signal or indirectly through variations in the airflow signal, may enable determination of the structures or factors contributing to sleep disordered breathing. Sound characteristics (e.g., presence of variation, amplitude, frequency, frequency range, harmonics, fundamentals, duration, volume) or timing relative to the respiratory cycle may enable similar determinations.

In another embodiment, determination of the anatomical structures or factors contributing to sleep disordered breathing using analysis of airflow or a combination of more than one signal may be used in the selection of treatments or prediction of the response to treatments. For example, the analyses performed in the determination of anatomical structures contributing to sleep disordered breathing may enable selection of structure-specific therapies. In addition, individuals with a greater peak airflow or greater degree of negative effort dependence during inspiration may respond more or less favorably to certain treatments.

Airflow and other data can be collected in any of multiple formats (e.g., analog, digital, etc.), and the analyses proposed can be performed in any of multiple manners (e.g., manual, automated, etc.).

Detecting and analyzing sleep disordered breathing may comprise the steps of monitoring airflow produced by a sleeping subject; identifying at least one of a snoring, hypopnea, or apnea event; and analyzing the identified snoring, hypopnea, or apnea event to locate upper airway structural sources of the event. This may include analysis of airflow during the event, before the events, after the event, or some combination of these time periods. The airflow analysis may include determination of peak inspiratory airflow rate, mid-inspiratory or plateau airflow rate, the ratio of peak inspiratory minus mid-inspiratory or plateau airflow rates to peak inspiratory airflow rate, change in airflow rates, or a combination of these and other measures. All or some of these steps may be performed by a processor programmed to receive airflow data, identify a sleep disordered breathing event, calculate these airflow or other measures, and output data.

It may be possible to identify at least one head and neck structure (or subtype) as a source of the snoring, hypopnea, or apnea event when the ratio content of the peak inspiratory minus plateau airflow rates to peak inspiratory airflow rate is substantially between a predetermined upper and lower ratio threshold specific to the head and neck structure (or subtype). This may determine the probability of response to a treatment.

An epiglottis may be a source of the snoring, hypopnea, or apnea event when there exists a decrease in the airflow rate during inspiration greater than a lower threshold decrease in rate. This may determine the probability of response to a treatment.

Peak inspiratory airflow rate may enable determination of the retropalatal or retrolingual cross-sectional area at end-expiration. This may determine the probability of response to a treatment.

Detecting and analyzing sleep disorders may include determination of variation in inspiratory or expiratory airflow, with this variation characterized with an amplitude and frequency. This variation may identify a snoring event. There may be monitoring of sound, with analysis of frequency, volume, and other sound wave characteristics.

It may be possible to identify at least one head and neck structure (or subtype) as a source of the snoring, hypopnea, or apnea event when the frequency content of the variation in airflow is substantially between a predetermined upper and lower frequency threshold specific to the head and neck structure (or subtype). This may determine the probability of response to a treatment.

A method of instructing a user may match the features of any embodiment described elsewhere in this application. For example, in another embodiment, a method may instruct a user to determine the anatomical structures or factors contributing to sleep disordered breathing using analysis of airflow. In another embodiment, a method may instruct a user to determine the anatomical structures or factors contributing to sleep disordered breathing with an examination of findings of fiberoptic endoscopy or other imaging technique and analysis of airflow, at least one other signal, or a combination of more than one signal. In another embodiment, a method may instruct a user to select a treatment for sleep disordered breathing or predict treatment outcome using analysis of airflow or a combination of airflow and at least one other signal.

A processor may be programmed to match the features of any embodiment described elsewhere in this application. For example, a processor may be programmed to receive airflow data characterizing a sleep disordered breathing event, to select at least one of a plurality of predefined airway structural sources associated with a sleep disordered breathing event based on a pattern defined by the data as outlined elsewhere in this application, and to output data indicative of the at least one of the plurality of predefined structural sources. The processor may be programmed to utilize known techniques (pattern matching, lookup tables, etc.) in the analysis of data. For example, a processor may be programmed to receive airflow data from an interval of at least 10 seconds associated with a sleep disordered breathing event, to characterize the sleep disordered breathing event with calculation of the ratio of peak inspiratory airflow rate minus mid-inspiratory airflow rate to peak inspiratory airflow rate, and to select at least one of a plurality of predefined airway structural sources based on the ratio via a lookup table that maps certain values or value ranges of the ratio to one or more of the predefined airway structural sources. In another embodiment, the processor may be programmed to output data indicative of at least one of a retropalatal or a retrolingual airway dimension based on data indicative of a peak inspiratory airflow rate via, for example, a lookup table that maps certain values or value ranges of the peak inspiratory airflow rate with certain dimensions. In another embodiment, the processor may be programmed to receive audio data characterizing a sleep disordered breathing event.

The processes, methods, or algorithms disclosed herein may be deliverable to or implemented by a processing device, controller, or computer, which may include any existing programmable electronic control unit or dedicated electronic control unit. Similarly, the processes, methods, or algorithms may be stored as data and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms may also be implemented in a software executable object. Alternatively, the processes, methods, or algorithms may be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for characterizing sleep disordered breathing comprising:

gathering inspiratory airflow data with a sensor during a sleep disordered breathing event; and determining by a processor, at least one of a plurality of predefined airway structural sources associated with the sleep disordered breathing event based on data indicative of a ratio of (i) a difference between a peak inspiratory airflow rate defined by the inspiratory airflow data and a mid-inspiratory airflow rate defined by the inspiratory airflow data to (ii) the peak inspiratory airflow rate; and outputting the at least one of a plurality of predefined airway structural sources associated with the sleep disordered breathing event.

2. The method of claim 1 wherein the determining is further based on data indicative of the peak inspiratory airflow rate.

3. The method of claim 1 wherein the determining is further based on data indicative of a plateau airflow rate defined by the inspiratory airflow data.

4. The method of claim 1 wherein the determining is further based on data indicative of the mid-inspiratory airflow rate.

5. The method of claim 1 wherein the determining is further based on data indicative of a ratio of (i) a difference between the peak inspiratory airflow rate and a plateau airflow rate defined by the inspiratory airflow data to (ii) the peak inspiratory airflow rate.

6. The method of claim 1 wherein the determining is further based on data indicative of a rate of change of inspiratory airflow rate defined by the inspiratory airflow data.

7. The method of claim 1 wherein the determining is further based on data indicative of at least one of a frequency of variation or an amplitude of variation in airflow rate defined by the inspiratory airflow data.

8. A method for characterizing sleep disordered breathing comprising:

gathering inspiratory airflow data with a sensor during a sleep disordered breathing event;

determining, by a processor, a selected one of a plurality of predefined airway structural sources associated with the sleep disordered breathing event based on data indicative of a rate of change of inspiratory airflow rate defined by the inspiratory airflow data; and outputting the selected one of a plurality of predefined airway structural sources associated with the sleep disordered breathing event.

9. The method of claim 8 wherein the determining is further based on data indicative of a peak inspiratory airflow rate defined by the inspiratory airflow data.

10. The method of claim 8 wherein the determining is further based on data indicative of a plateau airflow rate defined by the inspiratory airflow data.

11. The method of claim 8 wherein the determining is further based on data indicative of a mid-inspiratory airflow rate defined by the inspiratory airflow data.

12. The method of claim 8 wherein the determining is further based on data indicative of a ratio of (i) a difference between a peak inspiratory airflow rate defined by the inspiratory airflow data and a plateau airflow rate defined by the inspiratory airflow data to (ii) the peak inspiratory airflow rate.

13. The method of claim 8 wherein the determining is further based on data indicative of a ratio of (i) a difference between a peak inspiratory airflow rate defined by the inspiratory airflow data and a mid-inspiratory airflow rate defined by the inspiratory airflow data to (ii) the peak inspiratory airflow rate.

14. The method of claim 8 wherein the determining is further based on data indicative of at least one of a frequency of variation or an amplitude of variation in airflow rate defined by the inspiratory airflow data.

15. A method for characterizing sleep disordered breathing comprising:

gathering inspiratory airflow data with a sensor during a sleep disordered breathing event;

determining, by a processor, at least one of a retropalatal airway dimension or a retrolingual airway dimension associated with the sleep disordered breathing event based on data indicative of a peak inspiratory airflow rate defined by the inspiratory airflow data; and outputting the at least one of a retropalatal airway dimension or a retrolingual airway dimension associated with the sleep disordered breathing event.

* * * * *